(12) United States Patent
Kuroki

(10) Patent No.: US 11,895,254 B2
(45) Date of Patent: Feb. 6, 2024

(54) MOBILE TERMINAL DEVICE

(71) Applicant: COMFORT VISION RESEARCH LABORATORY Co. Ltd., Ebina (JP)

(72) Inventor: Yoshihiko Kuroki, Ebina (JP)

(73) Assignee: COMFORT VISION RESEARCH LABORATORY CO. LTD., Ebina (JP)

( * ) Notice: Subject to any disclaimer, the term of this patent is extended or adjusted under 35 U.S.C. 154(b) by 393 days.

(21) Appl. No.: 17/336,803

(22) Filed: Jun. 2, 2021

(65) Prior Publication Data

US 2021/0377371 A1 Dec. 2, 2021

(30) Foreign Application Priority Data

Jun. 2, 2020 (JP) ................................. 2020-096048

(51) Int. Cl.
| | | |
|---|---|---|
| *H04M 1/02* | (2006.01) | |
| *A61L 2/10* | (2006.01) | |
| *A61L 2/28* | (2006.01) | |
| *H04M 1/72* | (2021.01) | |
| *H04M 1/72403* | (2021.01) | |
| *H04M 1/17* | (2006.01) | |

(52) U.S. Cl.
CPC ............... *H04M 1/026* (2013.01); *A61L 2/10* (2013.01); *A61L 2/28* (2013.01); *H04M 1/72403* (2021.01); *A61L 2202/14* (2013.01); *H04M 1/17* (2013.01); *H04M 2250/22* (2013.01); *H04M 2250/52* (2013.01); *H04M 2250/54* (2013.01)

(58) Field of Classification Search
CPC .......... A61L 2/10; A61L 2/28; A61L 2202/14; H04M 1/026; H04M 1/17; H04M 1/72403; H04M 2250/22; H04M 2250/52; H04M 2250/54
See application file for complete search history.

(56) References Cited

U.S. PATENT DOCUMENTS

| | | | |
|---|---|---|---|
| 2016/0093412 A1 | 3/2016 | Liao et al. | |
| 2017/0266330 A1* | 9/2017 | Liao | .................... A61L 2/10 |
| 2019/0030196 A1* | 1/2019 | Bilenko | .................... A61L 2/10 |
| 2020/0085983 A1* | 3/2020 | Ramanand | ................ A61L 2/28 |

FOREIGN PATENT DOCUMENTS

| | | |
|---|---|---|
| CN | 106686164 A | 5/2017 |
| JP | 2006337195 A | 12/2006 |
| JP | 2016193045 A | 11/2016 |
| JP | 6317495 B1 | 4/2018 |
| KR | 101774748 B1 | 9/2017 |

OTHER PUBLICATIONS

JPO Office Action corresponding to JP Patent Application. No. 2020-096048, dated Jul. 28, 2021.

* cited by examiner

*Primary Examiner* — Mark R Gaworecki

(74) *Attorney, Agent, or Firm* — CANTOR COLBURN LLP

(57) ABSTRACT

A mobile terminal device including: an ultraviolet LED unit for irradiating an object with ultraviolet rays of a wavelength between 200 nm or more and less than 400 nm; an image sensor unit for capturing, as a ultraviolet irradiation region, the ultraviolet rays irradiated from the ultraviolet LED unit, an image sensor part for converting into image data the ultraviolet irradiation region captured by the image sensor unit; and a display and touch panel unit for displaying, as image information, the ultraviolet irradiation region converted into image data by the image sensor part.

2 Claims, 4 Drawing Sheets

MOBILE TERMINAL DEVICE

CROSS REFERENCE TO RELATED APPLICATIONS

This present invention claims priority under 35 U.S.C. § 119 to Japanese Patent Application No. 2020-096048, filed Jun. 2, 2020, the entire content of which is incorporated herein by reference.

TECHNICAL FIELD

The present invention relates to a mobile terminal device or personal data assistant (PDA) with ultraviolet irradiation and ultraviolet imaging functions.

BACKGROUND ART

Ultraviolet light is used to inactivate bacteria and viruses for the purpose of cleaning and disinfecting air and goods. In particular, it is generally known that ultraviolet light with a wavelength of about 200 nm to 400 nm inactivates bacteria and viruses. It is also known that ultraviolet light with a wavelength of 250 nm to 280 nm or 350 nm to 380 nm inactivates captured bacteria and viruses (see Patent Document 1, for example).

As a method of irradiating ultraviolet rays for the purpose of inactivating such bacteria and viruses, a portable ultraviolet irradiation device that irradiates ultraviolet rays with a wavelength of 200 nm to 400 nm only when the switch is pressed is also known (see Patent Document 2, for example).

Patent Document

Patent Document 1: JP-B-6317495
Patent Document 2: JP-A-2016-193045

SUMMARY OF INVENTION

Problem to be Solved by Invention

In an apparatus disclosed in Patent Document 1, as a relatively large air flow rate is assumed for the purpose of air purification, the device is required to be large and it is therefore difficult for a user to carry and use. In other words, such device is not suitable for easy disinfection and cleaning of personal belongings. In Patent Document 2, although miniaturization of the UV irradiation device has been achieved, it is not possible to confirm the actual state of irradiation due to the invisible nature of UV rays. In other words, it is not possible to recognize the irradiation status of the ultraviolet rays, which can easily lead to excessive irradiation or insufficient irradiation. The inability to recognize the irradiation of ultraviolet light may lead to a possibility of over-exposure to organs of a living body, and safety measures are required. Thus, with the conventional technology, there is no easy and safe way to inactivate the bacteria and viruses attached to the articles around us while checking the operation status.

In view of the above-mentioned problems of the prior arts, an object of the invention is to provide a mobile terminal device with portability, a high level of safety and a function of checking the status of ultraviolet irradiation.

In order to achieve the above-mentioned object, the present invention provides a mobile terminal device including: an ultraviolet LED unit for irradiating an object with ultraviolet rays of a wavelength between 200 nm or more and less than 400 nm; an image sensor unit for capturing, as a ultraviolet irradiation region, the ultraviolet rays irradiated from the ultraviolet LED unit; an image sensor part for converting into image data the ultraviolet irradiation region captured by the image sensor unit; and a display and touch panel unit for displaying, as image information, the ultraviolet irradiation region converted into image data by the image sensor part.

Preferably, the display and touch panel unit stores the image information of the ultraviolet irradiation region and displays an area displaying a movement trajectory of the ultraviolet irradiation region that is moved.

Preferably, the mobile terminal device further includes: a biometric recognition and determination unit for storing, as a minimum allowable distance, a minimum allowable distance for a living body to be irradiated from the UV LED unit, and for determining presence or absence of face, eyes, iris, pupils or skin of a living body; and an ultraviolet irradiation control part for irradiating the ultraviolet rays only when the face, eyes, iris, or skin of the living body is not present within the minimum allowable distance.

According to the present invention, a mobile terminal device with portability, a high level of safety and a function of checking the status of ultraviolet irradiation is provided.

BEST MODE FOR CARRYING OUT THE INVENTION

An embodiment of the present invention will be described below in detail with reference to the attached drawings. The invention is not limited to the following description, and may be modified as appropriate to the extent that it does not deviate from the gist of the invention.

Figure 1:
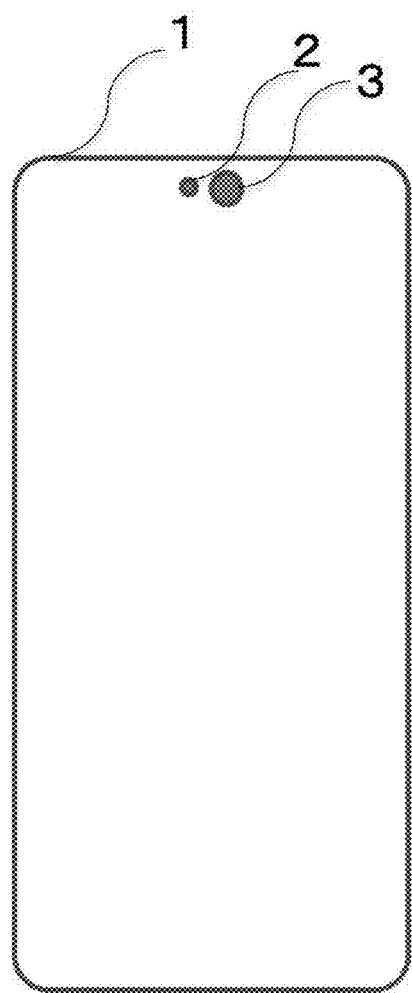
FIG. 1 is a rear view of the mobile terminal device according to the present invention.

FIG. 1 shows the backside of a mobile terminal device 1 of the present invention. On the back side of the device 1, there is an UV-LED unit 2 as a unit having a UV LED for irradiating ultraviolet rays from inside the mobile terminal device 1 and an irradiation lens for diverging the ultraviolet rays to a certain extent; and an image sensor unit 3 as a unit disposed near the UV-LED unit 2 and having an imaging lens and an image sensor sensitive to ultraviolet rays and visible light (normal light). Here, the region irradiated by the UV-LED unit 2 is within the imaging area of the image sensor unit 3.

Figure 2:
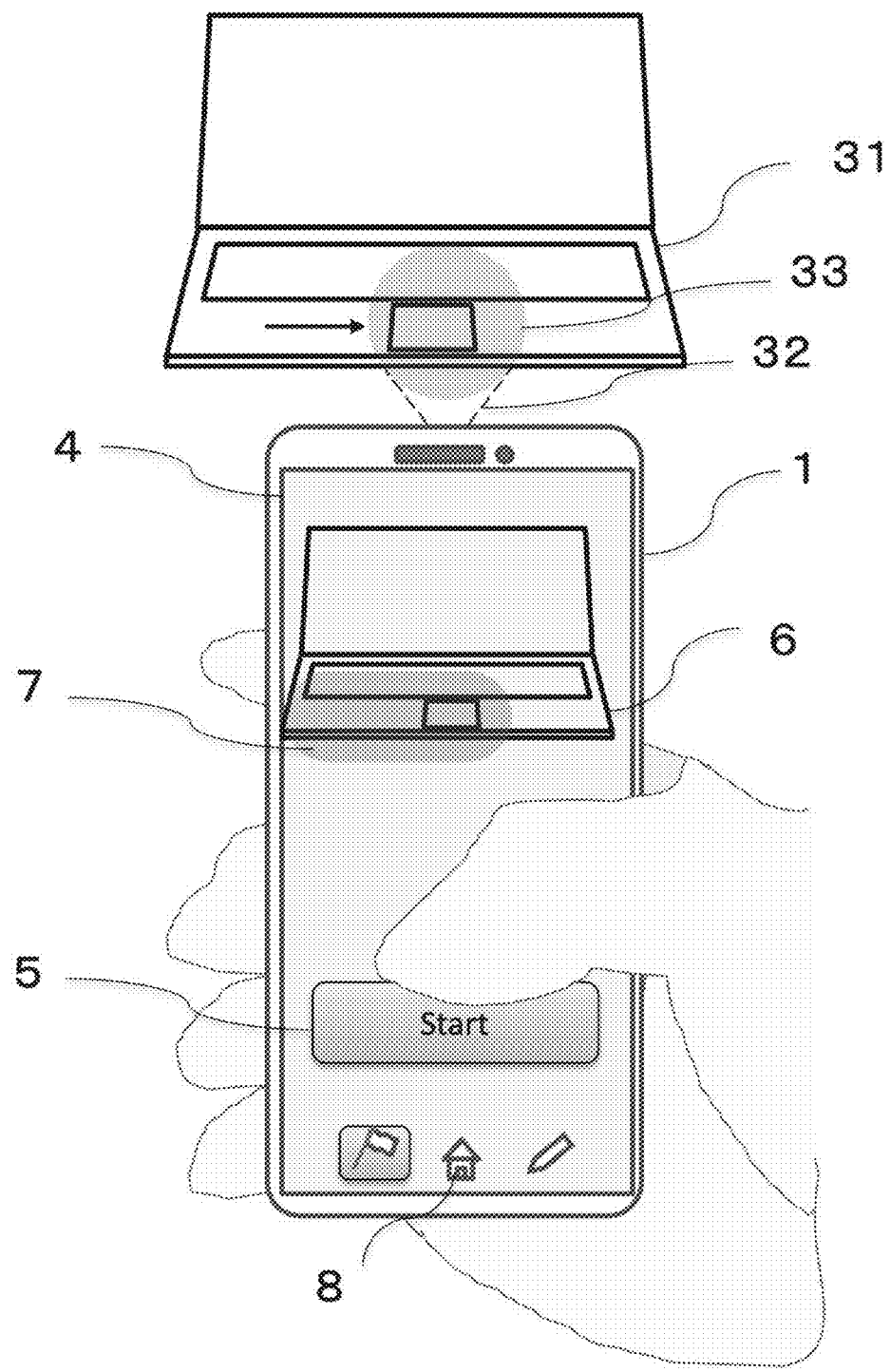
FIG. 2 is a front view of the mobile terminal device, illustrating the operating state of the mobile terminal device according to the present invention.

FIG. 2 shows the front side of the mobile terminal device 1 of the present invention. On the front side is disposed a display and touch panel unit 4 that includes a display panel unit 69 (described below) having a surface to which a transparent touch panel unit 66 (described below) is bonded. The display panel unit 69 displays the operation status of the application program. The display panel unit 69 also displays the UV irradiation control switch 5 for starting or stopping UV irradiation. In FIG. 2, the state of UV irradiation (that is, in such a state that a finger is in touch with the UV irradiation control switch 5 via the touch panel unit 66) is displayed. In an example shown in FIG. 2, an object 31 (personal computer, in this example) to be imaged and irradiated with ultraviolet light is displayed as display 6 on the display and touch panel unit 4. In addition, the area irradiated with ultraviolet rays is synthesized as a specific color into an image (the display 6) in normal light by a signal processing circuit 53 (to be described later) included in the main body via the image sensor unit 3 described above, and is stored and displayed as the display area 7. The display area 7 shows the region that has been irradiated with UV light as a trajectory. In addition, a menu switch 8 is displayed in the display unit 4, and the operation of the menu switch 8 allows inputting and terminating the initial setting values of the application program of the mobile terminal device 1.

The ultraviolet rays to be irradiated from the mobile terminal device 1 of the present invention to the object to be imaged 31 pass through the current UV irradiation path 32 (dashed line portion in FIG. 2) from the UV-LED unit 2 described above and irradiate the object to be imaged 31 as a current UV irradiation region 33. The user of the mobile terminal device 1 moves the present UV irradiation region 33 when irradiating the ultraviolet light on the object to be imaged 31 (e.g., in the arrow direction in FIG. 2).

The American Conference of Governmental Hygienists (ACGIH) and JIS Z8812 (method for measuring harmful ultraviolet radiation) are known as safety standards for ultraviolet rays. According to those standards, at a frequency of 253.7 nm, for example, the allowable illuminance that enables inactivation of bacteria and viruses but does not cause undesirable effects on the human body is 1 W/(m^2) for one minute of irradiation time and 60 W/(m^2) for one second of irradiation time.

The intensity of UV irradiation in the present invention is set in compliance with these safety standards. In addition, eyes of the human body in particular may develop conjunctivitis or keratitis when directly irradiated with ultraviolet light, and the skin may develop inflammation after a long period of intensive irradiation. Therefore, the present invention has a mechanism for irradiating ultraviolet light as a short pulse within the abovementioned limited time range only when there is no living body who approaches from a certain distance. In order to realize this mechanism, the present invention stores biometric information learned from patterns of the face, eyes, iris, pupils, skin, etc. in a second storage unit 56 (to be described later), and a biorecognition evaluation unit 60 (to be described later) executes signal processing to search for these patterns in the image captured by an image sensor function unit 52 (to be described later) for each frame of the image capture.

For face recognition, machine learning using neural networks, which take many normal human face images as input, is now relatively easy to achieve high-precision learning. However, because the pattern is based on the usual arrangement of eyebrows, eyes, nose, and mouth, the pattern information may be lost and the face may not be recognized when either half of the face is captured in approaching the full width of the screen or when the face is captured upside down. Therefore, the present invention considers the eyes and skin, which are particularly important safety measures in ultraviolet irradiation, and learns not only the face but also the whole of the eyes, the pattern of the iris and pupil, the color of the skin, and the pattern of the texture, etc., as various approaching and rotated images, and makes it possible to determine them as a living body.

Since the image sensor unit 3 and the UV-LED unit 2 are located near each other as described above, the distance L from the image sensor unit 3 to the object to be imaged 31 can be used as a substitute. There are several ways to obtain the distance L. The distance L can be obtained by using the image sensor unit 3 with a built-in shooting distance measurement function, by using a distance sensor near the image sensor unit 3 to obtain the distance L by signal processing that corresponds the output distance information to an image captured by the image sensor unit 3, or by calculating the distance L from the ratio of the size of a pattern of organs captured by the image sensor unit 3 to that of a known pattern of organs.

As a first method of obtaining the distance L, for example, in an image sensor unit having an autofocus function, the focal length that results in a focused image can be obtained by moving the lens slightly in the optical axis direction, so that the distance to the subject can be calculated from the focal length using a general lens formula. In addition, there are image sensor units that include a laser or an LED light source, and a method of measuring the distance to an object for each pixel can be used by detecting the flight time of the light from the light source to the image sensor when the light emitted from the light source is reflected by the object.

As a second method of obtaining the distance L, various types of distance sensors can be used, such as a type based on the above-mentioned time-of-flight or another type based on the change in the intensity of the reflection by irradiation of infrared light.

As a third method of obtaining the distance L, since there is a standard range of sizes of organs, such as for a human iris of about 11 mm to 12 mm, the known patterns of organs learned at various sizes and angles can be found in the image captured by the image sensor unit 3. The distance to the organ can be calculated using the formula of the relationship between the size of the object to be imaged and the distance to the object to be imaged.

As described above, in the present invention, the biorecognition evaluation unit 60 determines that the region to be irradiated with ultraviolet rays does not contain any organ such as a face or skin that is closer than the initial setting value Lmin stored in the first storage unit 55. An ultraviolet light control unit 61 controls an UV irradiation section 62, and a UV-LED drive circuit 64 drives a UV-LED unit 63 to irradiate ultraviolet rays for a period of time t. In order to contribute to the safety of the organs, it is desirable that the time t is not more than about 16 ms, which is one frame period when the frame rate of the imaging is 60 Hz.

The UV irradiation by the ultraviolet light control unit 61 and the UV irradiation section 62 is repeated while the UV irradiation control switch 5 is pressed, except when the stop mechanism described below operates, based on the recognition of the living body by the biorecognition evaluation unit 60 and the determination. In order to further improve the safety of the living body, the stop mechanism stops UV irradiation when the switch is kept pressed for more than duration T by counter C. The count frequency of this counter C is assumed to be 1 KHz, for example, and the count increases by one count every 1 ms, i.e., the period of time T is preferably a time corresponding to C=6,000 to C=3,000,000, i.e., about 1 minute or 5 minutes.

These values of the UV pulse irradiation time t, the minimum allowable distance Lmin to the living body, and the initial value 0 and maximum value Cmax of counter C, which limits the irradiation time, are stored in the first storage unit 55 (to be described later) as initial settings.

The relationship between the size of the object and the shooting distance can be obtained from the following equation:

Distance from the lens to the subject=(Lateral size of the area to be photographed)×(focal length of the lens)/(Lateral size of the image sensor)

If the focal length of the lens is 4 mm and the size of the image sensor is 6 mm, the distance from the lens to the subject is 200 mm when the entire object of 300 mm in the horizontal direction is reflected at the full horizontal size of the range of objects to be imaged. This calculation method may be used as a calculation method of obtaining the abovementioned irradiation distance of ultraviolet light, i.e., the distance L, from the ratio of the size of the pattern of the organs imaged by the image sensor unit 3 to the size of the pattern of the known organs stored in the second memory unit 56.

The angle of view of the lens of the UV-LED unit 2 for ultraviolet irradiation is preferably set at about ⅕ or ⅔ of the angle of view of the image sensor unit 3 so that the region of ultraviolet irradiation can be easily identified within the range of the image sensor unit 3 to be imaged.

In addition, the abovementioned determination that the potentially irradiated region does not contain any organs such as a pupil, iris, eye, face, skin, etc. of a certain size or larger is performed not only for the area of UV irradiation, but also for the entire area of imaging, i.e., the entire image angle of the image in the horizontal and vertical directions.

The above idea of safety is to keep the ultraviolet light intensity within the range of the safety standard even if the living body is directly irradiated with ultraviolet light, and to ensure safety, the irradiation distance to the body where the ultraviolet light intensity is attenuated by the inverse square law, that is, the distance L, is sufficiently secured. The minimum allowable distance L. i.e., the minimum allowable distance to an organ, Lmin, is preferably about 60 cm, for example.

Figure 3:
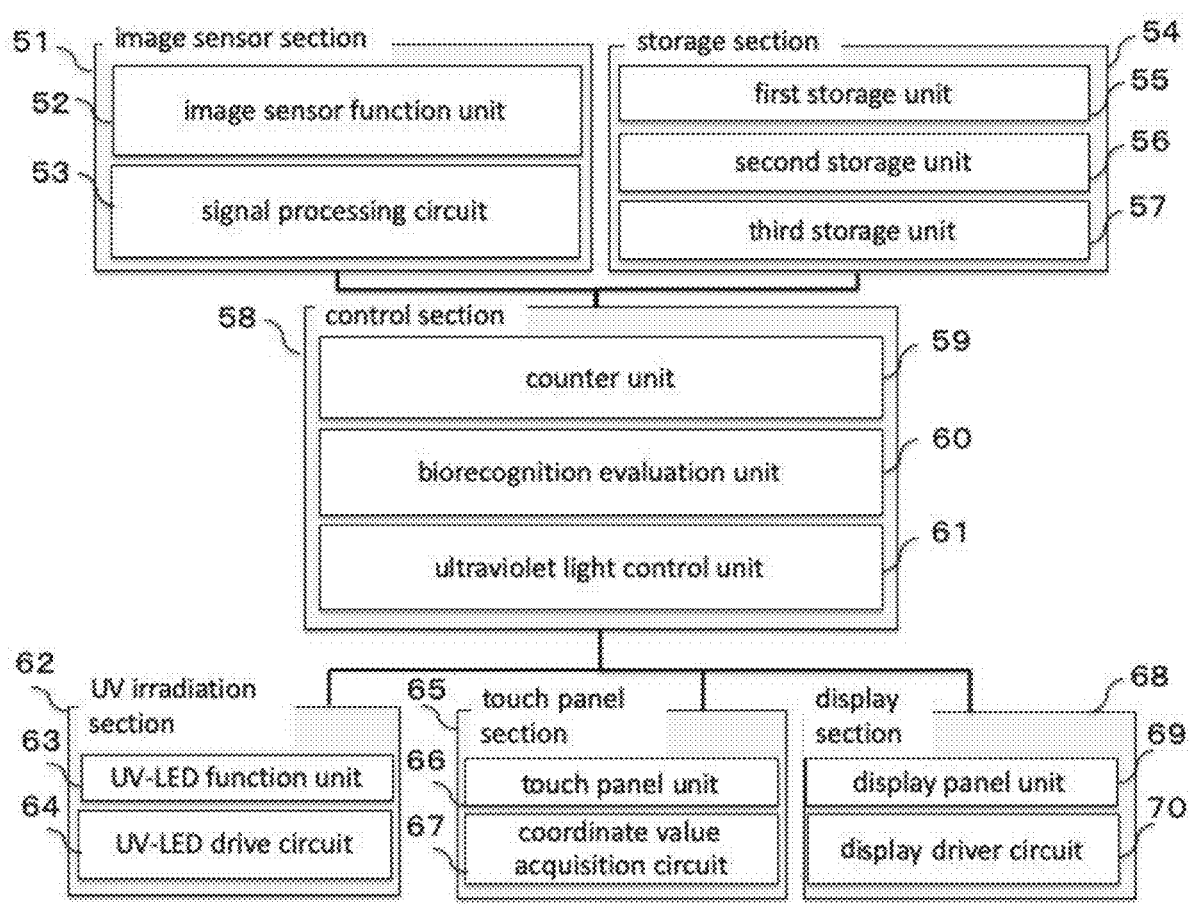
FIG. 3 is a block diagram, showing the configuration of the mobile terminal device according to the present invention.

FIG. 3 is a functional block diagram of the mobile terminal device 1. The mobile terminal device 1 includes an image sensor section 51, a storage section 54, a control section 58, the UV irradiation section 62, a touch panel section 65, and a display section 68. Main functions and relations of those sections are described as follows.

The image sensor section 51 is built in the vicinity of the image sensor unit 3 in the mobile terminal device 1, and mainly performs signal processing and imaging using ordinary light and ultraviolet light. The image sensor section 51 includes the image sensor function unit 52 for imaging ordinary light and ultraviolet light, and the signal processing circuit 53 for synthesizing ultraviolet light as a specific color into an image captured using ordinary light. As a result, the region irradiated with ultraviolet light (or which has been irradiated) in the display and touch panel unit 4 is visible as the display area 7 in a form that can be distinguished from other areas. Here, the image sensor function unit 52 includes the image sensor unit 3, which is a unit including an image sensor and a lens.

The storage section 54, which is built in the mobile terminal device 1, mainly stores initial setting values, biological information, and image frames captured by the image sensor section 51. The storage section 54 includes a first storage unit 55, second storage unit 56 and a third storage unit 57. The first storage unit 55 stores the initial setting values. The second storage unit 56 stores biometric information learned from patterns of face, eyes, iris, pupils, skin, and the like. The third storage unit 57 serves as a frame memory to temporarily store imaging information obtained by ordinary light and ultraviolet light.

The control section 58 is built in the mobile terminal device 1 and is mainly responsible for control corresponding to user operations, recognition of the image captured by the image sensor section 51, and control of ultraviolet radiation. The control section 58 includes: a counter unit 59 for counting the time during which the UV irradiation control switch 5 is pressed; a biorecognition evaluation unit 60 for recognizing and determining whether an organ is contained within the minimum allowable distance Lmin to the organ in the image; and the ultraviolet light control section 61 for controlling the UV irradiation time from the UV-LED unit 2 as t time.

The UV irradiation section 62 is built in the vicinity of the UV-LED unit 2 in the mobile terminal device 1 and irradiates the UV light in response to a signal mainly controlled by the control section 58. The UV irradiation section 62 includes the UV-LED function unit 63 to irradiate the UV light and the UV-LED drive circuit 64 as a driving circuit. Here, the UV-LED function unit 63 includes the UV-LED unit 2, which is a unit including a UV-LED and a lens.

The touch panel section 65 is built in the vicinity of the display and touch panel unit 4 in the mobile terminal device 1, and mainly serves as an interface for inputting user operations, and includes the transparent touch panel unit 66 installed on the front side of the display panel unit 69 and a circuit, i.e., the coordinate value acquisition circuit 67 for obtaining a coordinate value of a position touched on the surface and returning the result to the control section 58. In other words, when a user touches a menu or a switch displayed on the display panel unit 69 for operation, the finger of the user touches the touch panel unit 66, and the operation of the menu or the switch can be processed by obtaining the coordinate value of the touch panel unit 66.

The display section 68 is built in the vicinity of the display and touch panel unit 4 in the mobile terminal device 1, and mainly displays the image captured by the application program of the mobile terminal device 1, the ultraviolet irradiation region, the menu, etc. The display section 68 includes a display panel 69 and a display driver circuit 70 that drives the display panel unit 69.

Figure 4:
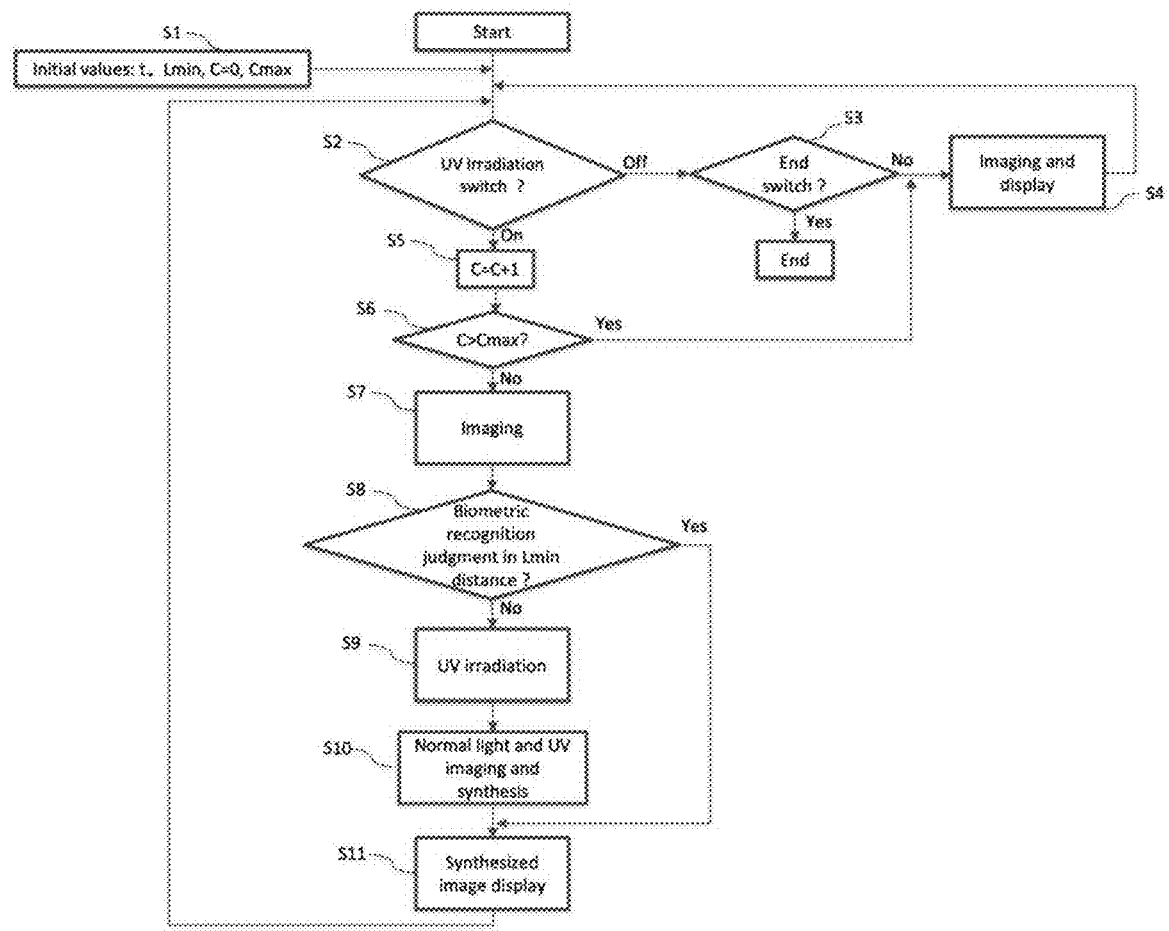
FIG. 4 is a flowchart, showing a flow of signal processing according to the present invention.

FIG. 4 is a flowchart, showing a flow of signal processing in the mobile terminal device 1. This process for signal processing is performed using the application program of the mobile terminal device 1. The steps of the process are described below.

First, in an initial setting read step S1, the UV irradiation time t, the minimum allowable distance to the living body or organ Lmin, the initial value of the counter C=0, and the maximum value of the counter Cmax, which were previously stored in the first storage unit 55 of the storage section 54 as initial settings, are read. Here, the initial value C=0 of the counter is remembered as a fixed value at the time of shipment from the factory of the mobile terminal device 1, but the UV irradiation time t, the minimum allowable distance to the living body Lmin, and the maximum value Cmax of the counter can be input, according to the user's environment, by the user operating the menu switch 8 of the application program in the mobile terminal device 1. However, as mentioned above, the fact that t is recommended to be 1 ms to 16 ms, Lmin is recommended to be 60 cm, and Cmax is recommended to be 6,000 to 3,000,000 is conveyed to the user as a message when operating the menu switch 8 of the application program in the mobile terminal device 1.

Next, in a UV irradiation switch determination step S2, the state of whether the UV irradiation control switch 5 is pushed is determined by the coordinate value acquisition circuit 67 in the touch panel section 65 via the touch panel unit 66. If the state of this switch, i.e., the determination result, is On, the process goes to a counter value addition step S5 as the next step, and if the switch is Off, the process goes to an end switch determination step S3.

In a counter value incrementing step S5, the counter C is incremented by one by the counter unit 59 of the control section 58 which counts the time during which the UV irradiation control switch 5 is pressed.

In a counter maximum value determination step S6, it is determined whether the value of the counter C exceeds the maximum value of Cmax, and if the result is Yes, the process proceeds to an imaging and image display step S4, and if the result is No, the process proceeds to an imaging step S7. If the result is Yes, it means that the counter C exceeds Cmax. Therefore, the ultraviolet light is not irradiated for safety, the display of the image is continued for ease of use, and a message is displayed to the user by the application program of the mobile terminal device 1 urging the user to terminate the program once. By terminating the program once and starting the program again, the user can initialize the counter C with the initial value C=0 stored in a first storage unit 55 and return to a normal state of use.

In the imaging step S7, the image sensor unit 3 in the image sensor function unit 52 of the image sensor section 51 performs the imaging. As a result, the image of the object to be imaged 31 is passed to the signal processing circuit 53 of the image sensor section 51.

In the biometric recognition determination step S8, the biorecognition determination unit 60 of the control section 58 performs bio-recognition determination to judge whether an organ is included within a minimum allowable distance Lmin within a distance L from the image sensor unit 3 of the image sensor function unit 52 to the object to be imaged 31, using the bio-recognition information stored in the second storage unit 56 from the image captured in the imaging step S7. This distance L is equivalent to the distance from the UV-LED unit 2 to the object to be imaged 31 as described above. As a result of this recognition determination, if an organ is within Lmin, or if Yes, the process proceeds to a synthesized image display step S11, and if No, the process proceeds to the UV irradiation step S9.

In the UV irradiation step S9, the UV-LED unit 2 in the UV-LED function unit 63 of the UV irradiation section 62 is controlled by the ultraviolet light control unit 61 and driven by the UV-LED drive circuit 64 to irradiate the UV light as a pulse for time t. In this way, the ultraviolet light is irradiated to the object to be imaged 31. In addition, the ultraviolet light is not irradiated from the UV-LED unit 2 by the ultraviolet light control unit 61 if there is an organ or living body within the minimum allowable distance Lmin according to the step S8.

In a step S10, in the signal processing circuit 53 of the image sensor section 51, the images of the normal light and the ultraviolet light are captured, and the composite image is then generated by the signal processing circuit 53 of the image sensor section 51, and the image information of the normal light and the ultraviolet light is stored in the third storage unit 57 of the storage section 54.

In the synthesized image display step S11, the synthesized image generated in the step S10 is displayed on the display panel unit 69 of the display and touch panel unit 4 using the display driver circuit 70 in the display section 68. As a result, the UV irradiation region 33 is displayed on the display panel unit 69 as the display area 7 in the display 6. As a result, the user can see the area irradiated with ultraviolet rays through the display and touch panel unit 4. Then, the process returns to the step S2, and the above-mentioned operation is repeated.

In the end switch determination step S3, the state of the end switch displayed by the user operating the menu switch 8 of the application programs of the mobile terminal device 1 is determined. When the end switch is finally pressed, that is, when Yes, the process of the application program is terminated, and when No, the process proceeds to the UV irradiation switch determination step S2.

In addition, in the synthesized image display step S11 that is repeatedly performed, if the position of the UV irradiation region 33 is different from the position of the UV irradiation region 33 in the previous synthesized image display step S11, the ultraviolet irradiation display is combined with an ordinary imaging image and then stored and displayed as the display area 7 (that is, the area to which the ultraviolet radiation is irradiated is displayed on the display and touch panel unit 4 as the display area 7 as a trajectory). This operation is performed as follows.

The imaging area before by one unit time, such as one frame of ultraviolet and normal light, is divided into small areas, such as 32 pixels by 32 pixels. Since the same subject in each successive frame exists nearby in the captured image due to the continuity of video capture, it can be assumed that a small area in the captured image at the present time is included in a search area of, for example, 128 pixels by 128 pixels as centered around the small area.

In this way, the movement of the same subject can be recognized by finding the closest region in the search region at the current time by search matching of the differences, as mathematical distances, in pixel information, using the previous small region one unit time ago as a template.

The method of search matching described above can be arbitrarily selected, such as the method in which the total sum of the differences in RGB for the number of pixels in the abovementioned small region is the distance, or the method in which the correlation for the pixels is the distance.

The method of storing and displaying the image sensor output for the UV irradiation region 33 at the current time as shown in the display area 7 when the movement of the same subject between successive frames is tracked by an ordinary visible light image as described above will be described below.

In order to easily display the ultraviolet rays included in the output of the image sensor unit 3, for example, purple is assigned as a specific color, and the image of the ultraviolet rays are added and synthesized with a certain degree of transparency to the image captured by the image sensor unit 3 in normal light and displayed. At this time, the output of the normal light portion and the ultraviolet portion of the image sensor unit 3 is stored in the third storage unit 57, i.e., the frame memory, for later use.

Thus, since the movement of the same subject is known between the above-mentioned continuous frames and the ultraviolet portion irradiated by the UV-LED unit 2 one unit time ago is stored in the third storage unit 57 together with the image captured by the normal light, the pixel information that is the output of the ultraviolet portion of the image sensor unit 3 at the present time is added by the signal processing circuit 53 to the pixel information that is the output of the ultraviolet portion of the image sensor unit 3 one unit time ago of the same subject whose movement is known in the third storage unit 57 and displayed, and the display area 7 of the ultraviolet irradiation region can be displayed.

By utilizing the technologies of ordinary visible light imaging, image display, and touch panel functions that are already provided in mobile terminal devices that are widely used as consumer products, and by adding UV LEDs, image sensors that are sensitive to UV light, and signal processing technologies, it is possible to contribute to the widespread use of devices that realize simple and safe inactivation of bacteria and viruses.

The invention claimed is:

1. A mobile terminal device, comprising:
    an ultraviolet LED unit for irradiating an object with ultraviolet rays of a wavelength between 200 nm or more and less than 400 nm;
    an image sensor unit for capturing, as an ultraviolet irradiation region, the ultraviolet rays irradiated from the ultraviolet LED unit;
    an image sensor part for converting into image data the ultraviolet irradiation region captured by the image sensor unit; and
    a display and touch panel unit for displaying, as image information, the ultraviolet irradiation region converted into image data by the image sensor part,
    wherein the display and touch panel unit stores the image information of the ultraviolet irradiation region and displays an area displaying a movement trajectory of the ultraviolet irradiation region that is moved.

2. The mobile terminal device according to claim 1, further comprising:
    a biometric recognition and determination part for storing, as a minimum allowable distance, a minimum allowable distance for a living body to be irradiated from the UV LED unit, and for determining presence or absence of face, eyes, iris, pupil or skin in the living body; and
    an ultraviolet irradiation control part for irradiating the ultraviolet rays only when the face, eyes, iris, or skin in the living body is not present within the minimum allowable distance.

* * * * *